(12) United States Patent
Fusaro et al.

(10) Patent No.: US 8,596,118 B2
(45) Date of Patent: Dec. 3, 2013

(54) HTA FLUID LEVEL AND FLUID TYPE MEASUREMENT

(75) Inventors: Michael P. Fusaro, Greenville, RI (US); Greg Johnston, Portland, ME (US); Stephen S. Keaney, Groton, MA (US); Boris Shapeton, Westwood, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/420,202

(22) Filed: Mar. 14, 2012

(65) Prior Publication Data

US 2012/0167678 A1   Jul. 5, 2012

Related U.S. Application Data

(63) Continuation of application No. 12/277,440, filed on Nov. 25, 2008, now Pat. No. 8,146,420.

(60) Provisional application No. 61/016,168, filed on Dec. 21, 2007.

(51) Int. Cl.
  *G01F 23/24* (2006.01)

(52) U.S. Cl.
  USPC ........................................ 73/304 R

(58) Field of Classification Search
  USPC ............................................ 73/304 R, 304 C
  See application file for complete search history.

(56) References Cited

U.S. PATENT DOCUMENTS

| | | | |
|---|---|---|---|
| 7,584,656 B2* | 9/2009 | Senghaas et al. | 73/170.21 |
| 7,905,144 B2* | 3/2011 | Thobe | 73/304 R |
| 8,146,420 B2* | 4/2012 | Fusaro et al. | 73/304 R |
| 2005/0229700 A1* | 10/2005 | Chai et al. | 73/304 R |
| 2006/0021432 A1* | 2/2006 | Salzmann et al. | 73/304 R |
| 2008/0097563 A1* | 4/2008 | Petrie et al. | 607/105 |

* cited by examiner

*Primary Examiner* — Hezron E Williams
*Assistant Examiner* — Paul West
(74) *Attorney, Agent, or Firm* — Fay Kaplun & Marcin, LLP

(57) ABSTRACT

Apparatus for measuring an amount of ablation fluid circulating in a system for ablating tissue comprises a plurality of electrical contacts located within an ablation fluid receiving chamber of the system, the contacts being located at various heights and a data processing arrangement coupled to the contacts to receive data corresponding to electrical conductance between pairs of the contacts, the data processing arrangement determining a height of fluid in the chamber based on the measured conductance levels and determining based on the determined height, whether an amount of fluid circulating through the system is within a desired range.

7 Claims, 4 Drawing Sheets

HTA FLUID LEVEL AND FLUID TYPE MEASUREMENT

PRIORITY CLAIM

The present application is Continuation application of U.S. patent application Ser. No. 12/277,440 filed on Nov. 25, 2008, now U.S. Pat. No. 8,146,420; which claims the priority to U.S. Provisional Application Serial No. 61/016,168 filed on Dec. 21, 2007. The entire disclosures of the above applications are expressly incorporated herein by reference.

BACKGROUND

Menorrhagia, excessive uterine bleeding during a prolonged menstrual period, has been attributed to disorders of the endometrium. While hysterectomies provides a definitive treatment for menorrhagia, less invasive procedures are attractive as they generally entail reduced side effects, shorter hospital stays and less procedural and post-operative discomfort.

Generally, these less invasive procedures ablate tissue through the application of electrical energy (e.g., RF energy), heat (e.g., laser) or cryogenic temperatures. However, these procedures typically rely on direct visualization of the uterus by an experienced operator to ablate selected portions of the endometrium. Alternatively, the entire endometrium may be treated by conduction uterine ablation, i.e., circulating a heated fluid through the uterus. In certain of these procedures, the heated fluid may be contained within a balloon while circulating through the uterus while in others, the fluid directly contacts the endometrium. These systems generally employ a resistive element to heat the ablation fluid (e.g., saline) to a temperature within a desired range while maintaining the pressure of the circulated fluid substantially constant.

SUMMARY OF THE INVENTION

The present invention is directed to an apparatus for measuring an amount of ablation fluid circulating in a system for ablating tissue, comprising a plurality of electrical contacts located within an ablation fluid receiving chamber of the system, the contacts being located at various heights and a data processing arrangement coupled to the contacts to receive data corresponding to electrical conductance between pairs of the contacts, the data processing arrangement determining a height of fluid in the chamber based on the measured conductance levels and determining based on the determined height, whether an amount of fluid circulating through the system is within a desired range.

DETAILED DESCRIPTION

The present invention may be further understood with reference to the following description and the appended drawings. Although the present invention relates to systems and methods for measuring fluid level and detecting fluid properties within a device for thermally ablating the endometrium, the devices and methods according to the present invention and components thereof may be utilized in conjunction with systems for prostate treatment (microwave or cryoablation), irrigation systems or any other fluid ablation devices.

Thermal ablation is more safe, effective and efficient when flow level and pressure within the hollow organ are precisely controlled to desired levels. As those skilled in the art will understand, the exact values of flow levels and pressures may vary in accordance with, for example, patient conditions, the procedure to be performed, etc.

Figure 2:
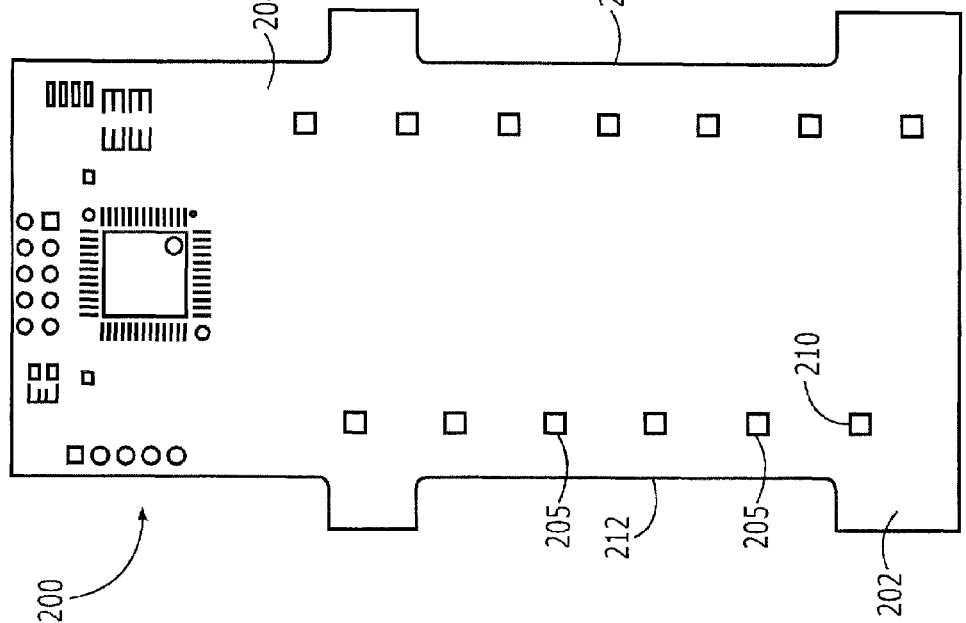
FIG. 2 shows a second view of a first design for an exemplary embodiment of the present invention.
Figure 1:
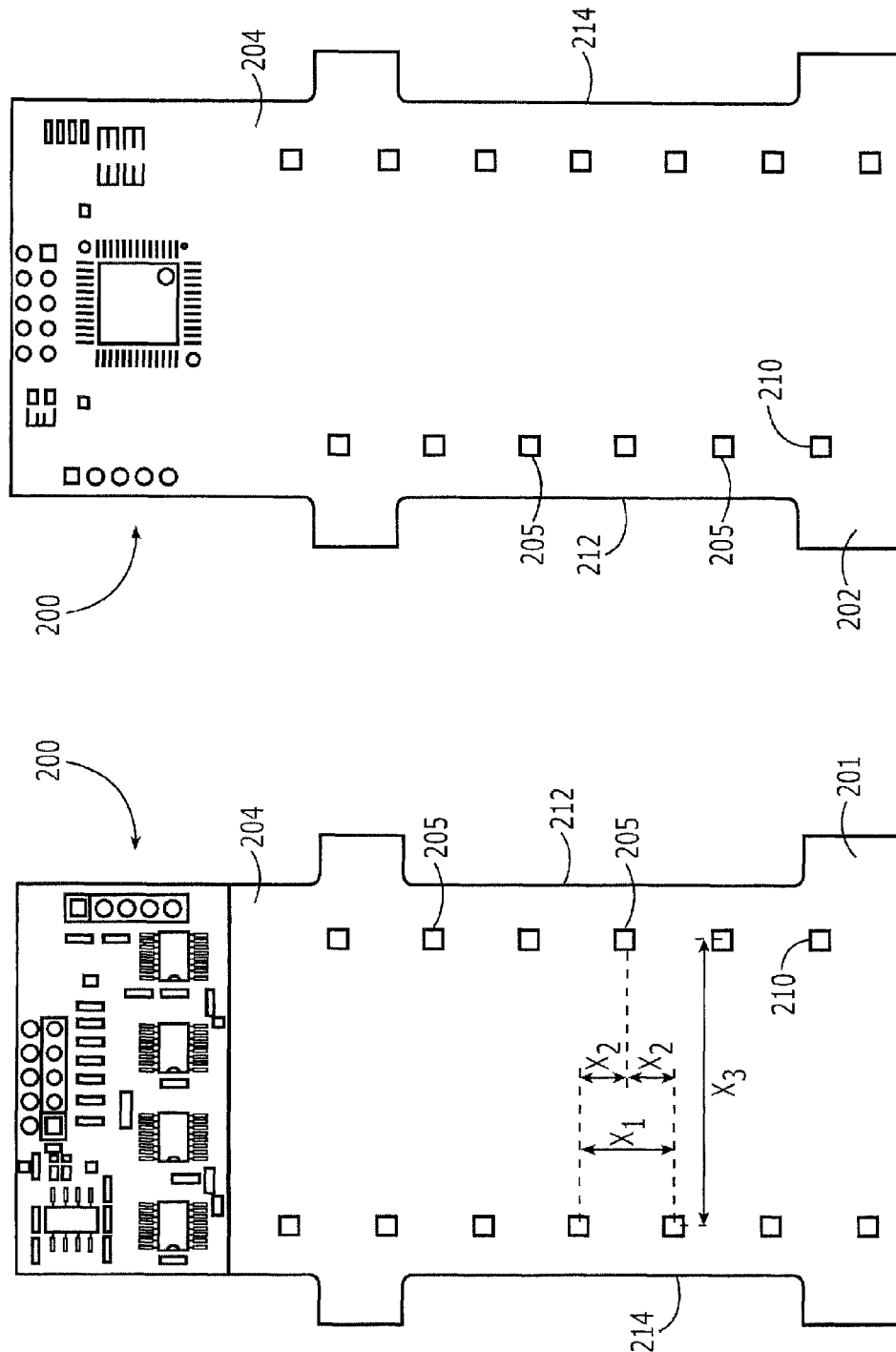
FIG. 1 shows a first view of a first design for an exemplary embodiment of the present invention.
Figure 3:
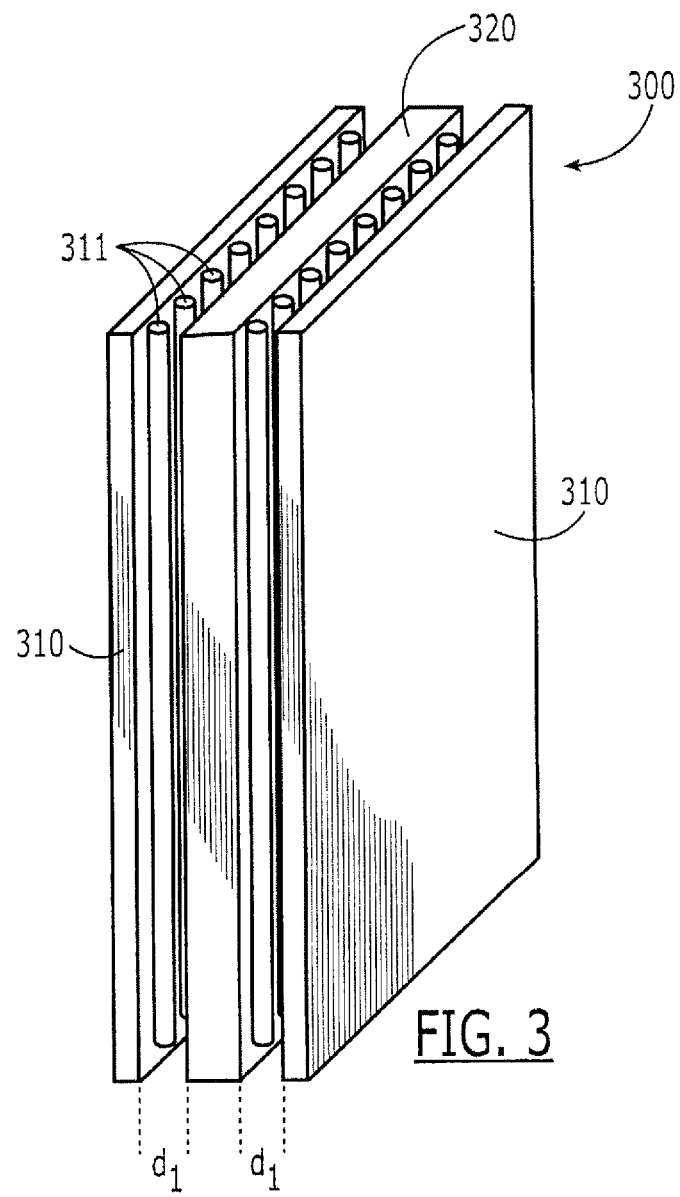
FIG. 3 shows a first design for a second exemplary embodiment of the present invention.

The present invention employs a processing unit comprising a set of elements which, when operating in conjunction with one another, accurately measure a level and detect a type of fluid circulating within a thermal ablation system. For example, one such system is described in the U.S. Patent Application Ser. No. 60/987,913, entitled "Thermal Ablation System", naming as inventors Robert J. Bouthillier, Michael P. Fusaro, Joseph M. Gordon, Stephen S. Keaney, Brian MacLean, Andrew W. Marsella, David Robson and Boris Shapeton filed on Nov. 14, 2007. The entire disclosure of this application is hereby incorporated by reference herein. As shown in FIGS. 1 and 2, a Conductive Level Sensor 200 according to a first exemplary embodiment of the invention is situated, for example, on a surface of a printed circuit board ("PCB") 204. As would be understood by those skilled in the art, the Conductive Level Sensor 200 may be formed as a separate chip or incorporated into a processing unit also comprising a microprocessor or other data processing arrangement.

The ablation system according to this embodiment is a closed loop system for recirculating fluid from the apparatus into the uterus and back to the system with the Conductive Level Sensor 200 located within a fluid chamber (not shown) of the ablation system. The Conductive Level Sensor 200 is arranged vertically so that, as the amount of ablation fluid circulating through the system varies, the level of fluid in the chamber rises and falls moving an upper surface of the fluid up and down the surface of the Conductive Level Sensor 200. As will be described in more detail below, the Conductive Level Sensor 200 detects the level of the fluid in the chamber and the conductivity of the ablation fluid, The Conductive Level Sensor 200 or a separate processing unit then compares the detected fluid level and conductivity to desired values or desired ranges of values and takes actions based on the comparison.

The Conductive Level Sensor 200 includes a plurality of contacts 205 (e.g., gold-plated contacts) which are formed in an array substantially uniformly spaced in vertical columns along front and back surfaces 201, 202, respectively of the PCB 204. However, those skilled in the art will understand that the contacts 205 may be formed of any other suitable conductive material and arranged in any desired pattern at selected heights corresponding to various amounts of fluid circulating through the system. For example, depending on the geometry of the fluid chamber within which the PCB 204 is arranged, changes in the height of the upper surface of the ablation fluid may correspond to varying volumetric differences along the height of the PCB 204. In such a case it may be desirable to space the contacts 205 vertically at locations corresponding to equal volumetric differences. The contacts 205 are arranged in lines adjacent to left and right edges of the PCB 204 and each have a diameter of approximately 0.02 inches. Vertical columns of the contacts 205 spaced from one another by a length $X_1$ of approximately 0.02 inches. The contacts 205 are vertically spaced from adjacent contacts 205 by a length $X_2$ of approximately 0.05 inches Furthermore, the vertical columns 210 are horizontally spaced a length $X_3$ of approximately 0.06 inches from one another. Those skilled in the art will understand that the vertical spacing of the contacts 205 determines the resolution of the measurement—i.e., the minimum system volume differential which can be detected.

Furthermore, as described in more detail below, by staggering the contacts 205 in the two columns so that contacts in the left hand column are vertically between contacts 205 of the right hand column, the resolution is further increased. The contacts 205 are also preferably situated on front 201 and rear 202 sides of the PCB 204 in order to avoid film effects, as would be understood by those skilled in the art.

As described above, the contacts 205 are conductive, allowing the processing arrangement to utilize an array of analog switches to measure the conductivity between pairs of the contacts 205 with the ablation fluid (e.g., saline) serving as a conductor. The conductivity measurements provided by the Conductive Level Sensor 200 may thereby be employed by the processing arrangement to determine properties of the fluid circulating through the system. Specifically, the processing arrangement correlates the measured conductivity reading to a baseline conductivity value (or range of values) associated with desired properties of the ablation fluid (e.g., level of salinity), If the measured conductivity value falls outside of the acceptable range, the processing arrangement may determine that a fluid other than the desired fluid has been introduced into the system. Accordingly, when conductivity ranges detected for the ablation fluid fall outside a predetermined range, the system may generate an alert to a user indicating that the proper fluid has not been supplied. Alternatively, when such a condition is detected, the system may execute a safe procedure (e.g., terminating the procedure or suspending the procedure until a fluid having the desired properties is supplied).

As described above with respect to the front and rear sides 201, 202, respectively, of the Conductive Level Sensor 200, the exemplary embodiment has two separate analog switch test paths measuring conductivity between pairs of the contacts 205 in a first direction A. The Conductive Level Sensor 200 employs at least two separate test paths to allow for greater accuracy in the conductivity reading. Specifically, a first set of measurements may be made between corresponding sets of conductors 205 located on the front side 201 and sets of conductors located on the rear side 202 adjacent a first edge 212 of the PCB 204. The first set of measurements may follow the direction A until each set of conductors has performed a measurement. A second set of measurements may be made between corresponding sets of conductors 205 located on the front side 201 and sets of conductors located on the rear side 202 adjacent a second edge 214 of the PCB 204, also in direction A. The first and the second set of measurements may then be compared to one another by the processing arrangement to ensure the validity of the readings. If the readings differ from one another by a value greater than a predetermined threshold, a user may be notified of the error or the system may automatically execute a safety procedure.

Additionally, two test components may be situated between the at least two analog switch test paths as described earlier to check the system for any or all of a plurality of errors including, among others, the detection of a fluid other than saline as described above. A fault may be indicated to the processing arrangement via a sequence of pulse-width modulated signals along a digital output line. The Conductive Level Sensor 200 may define different pulse sequences for each type of fault. For example, the Conductive Level Sensor 200 may define three pulse sequences: one pulse sequence for situations where fluid properties detected correspond to those of the desired ablation fluid, a second for situations where the detected fluid properties are outside the preset range and a third pulse sequence signifying one or more other faults in the system. Those skilled in the art will understand that various alternate pulse sequences may be introduced without deviating from the scope of the present invention.

Figure 4:
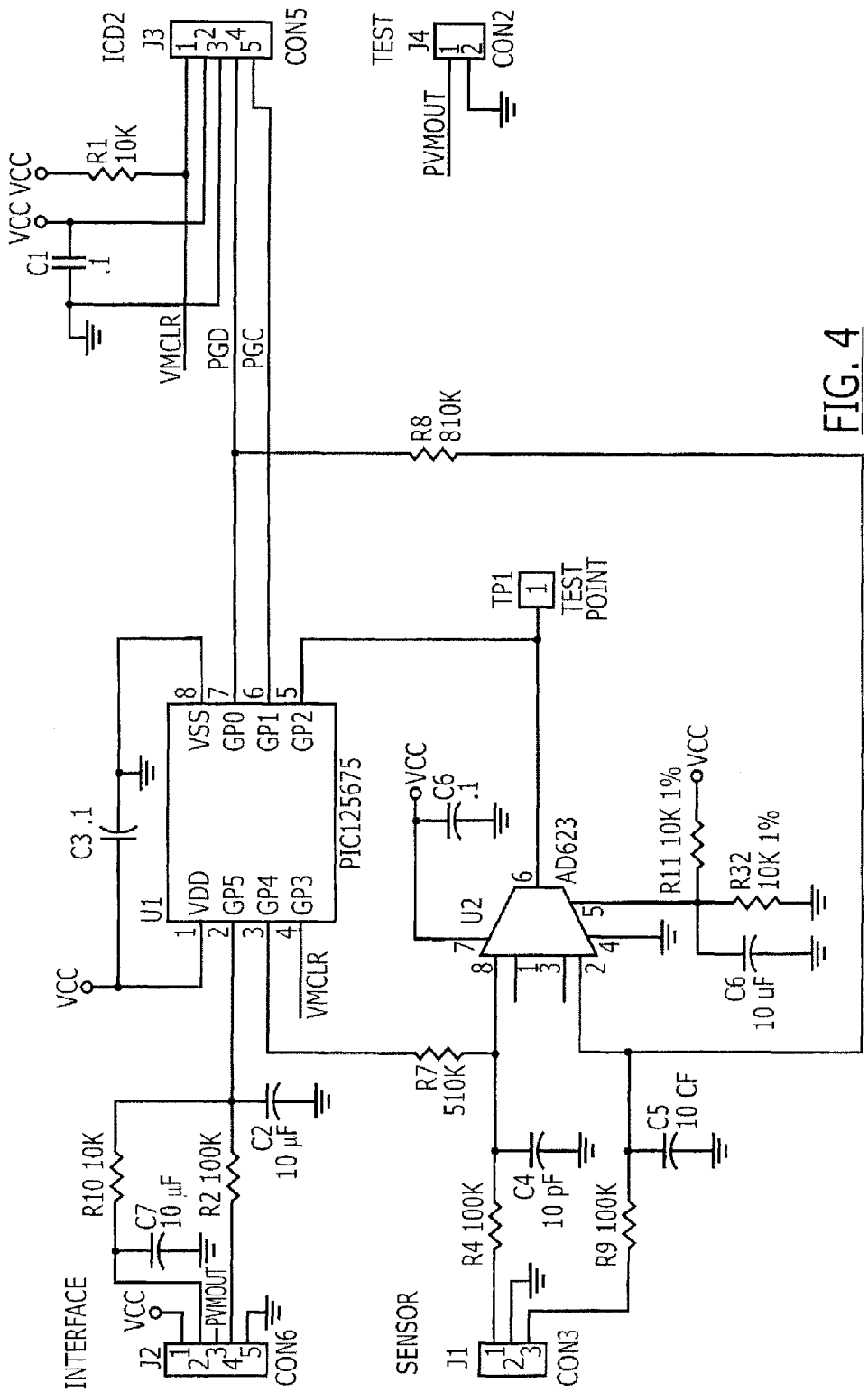
FIG. 4 shows the circuitry for a second exemplary embodiment of the present invention.

An alternate embodiment of the present invention employs a Capacitive Level Sensor 300 to detect the fluid level and fluid properties. The Capacitive Level Sensor 300 is preferably seated within the manometer of a disposable cassette of a thermal ablation device. That is, certain ablation systems include a reusable console and a disposable cartridge with all of the fluid contacting surfaces of the device being included within the disposable cartridge so that the console may be reused without the need for sterilization, etc. The Capacitive Level Sensor 300 comprises a PCB which, when immersed in the manometer of the cassette of the thermal ablation device, is in contact with the saline fluid. Capacitive elements as shown in the circuit diagram of FIG. 4 are built into the PCB, which, for example, comprises a plurality of copper plates 310 over a surface thereof. Accordingly, no external sensor elements are required as the capacitance may be measured through the conductive copper of the copper plates 310. It is noted that although the exemplary embodiment is described with respect to copper plates, any alternate conductive material may be used, as those skilled in the art will understand.

The Capacitive Level Sensor 300 measures changes in capacitance of sensor strips 311 as fluid fills the cassette of the thermal ablation device and the level of the fluid moves up along the surface of the PCB. The change in capacitance is then used by a processing arrangement of the Capacitive Level Sensor 300 to determine the level of fluid in the cassette of the thermal ablation device and to determine, based on this level, an amount of fluid circulating through the system.

Figure 5:
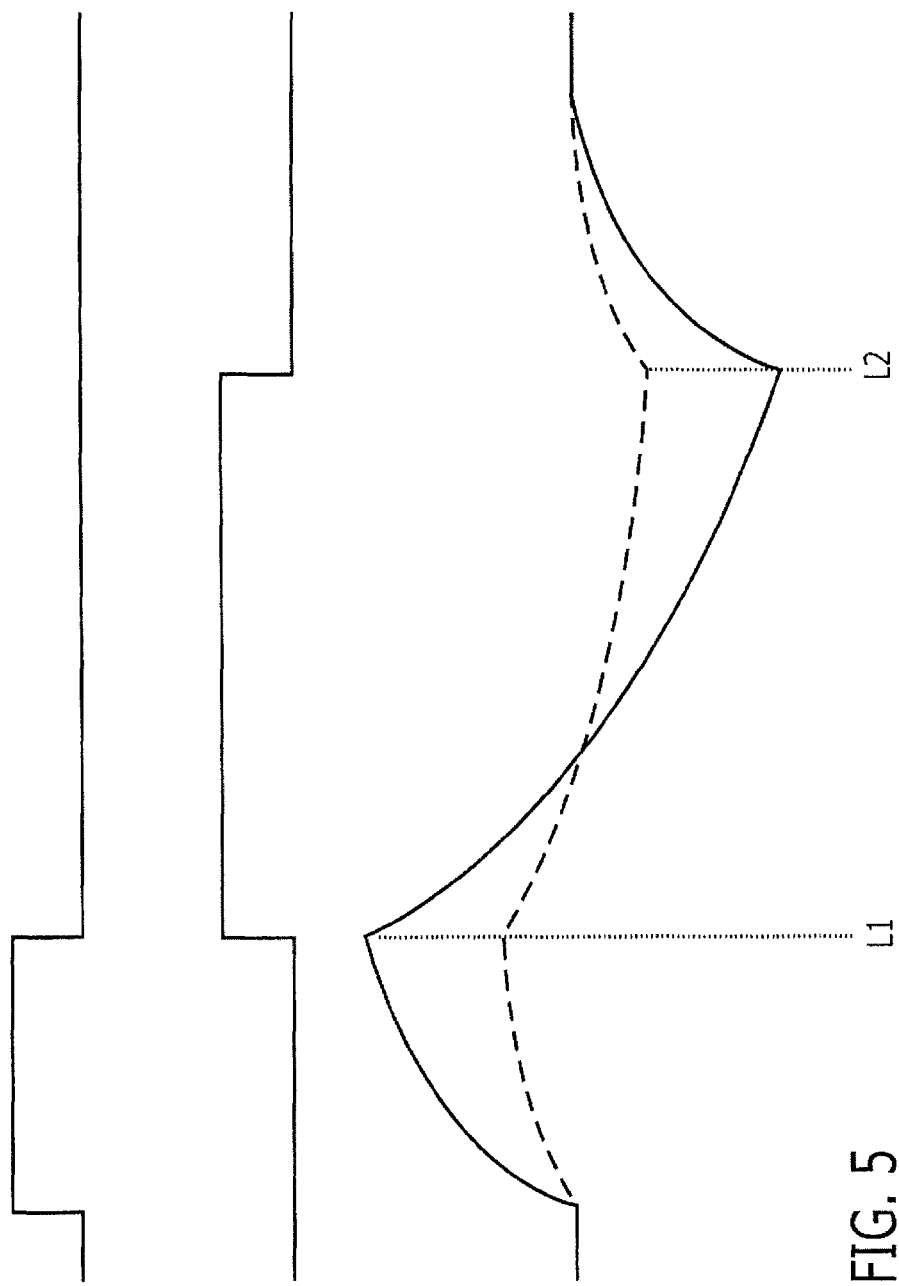
FIG. 5 details the method of the second exemplary embodiment of the present invention.

A Level-Sense Processor Board of the Capacitive Level Sensor 300 injects a pulse into the ablation fluid and performs a synchronized measurement of the amplitude of the resulting waveform using a differential amplifier. As shown in FIG. 5, the two inputs for the differential amplifier may be Pulse A and Pulse B, as those skilled in the art will understand. The resulting waveform, L1, will be indicative of the capacitance of the ablation fluid. Those skilled in the art will understand that the L1 value may include common-mode effects such as stray noise. Since this noise voltage is a common component of both input voltages Pulse A and Pulse B, the noise, indicated by L2, will be canceled out when a difference between the amplifier inputs is taken. The capacitance of the ablation fluid, L, may then be calculated using the formula L=L1−L2.

The resulting pulse waveform L (not shown) is then indicative of the capacitance of the ablation fluid without noise interference. Thus, the L value indirectly indicates an amount of fluid present in the cassette of the thermal ablation device which is directly related to the amount of fluid flowing through the system. As those skilled in the art will understand, if the amount of fluid in the cassette increases, the L value increases proportionally. Accordingly, the L value may be used to determine the amount of fluid in the cassette and determine thereby whether an obstruction is blocking fluid flow or there has been a loss of fluid (i.e., by absorption into the body or leakage), etc.

Those skilled in the art will understand that the capacitance of the fluid which directly affects the L value, may be affected by a number of variables including, but not limited to, the thickness of the Capacitive Level Sensor's 300 outer layer and the surface area of the externally applied copper plates 310 of the Capacitive Level Sensor 300. Accordingly, it is necessary to account for these values when determining the capacitance of the ablation fluid.

The capacitance of the externally applied plates 310 of the Capacitive Level Sensor 300 may be calculated in two steps. In the first step, the capacitance of the empty Capacitive Level Sensor 300 may be calculated using the following formula:

$$C_1 = (0.118 * K_1 A_1) d_1$$

where $C_1$ refers to the capacitance, $K_1$ refers to the dielectric constant of an insulator situated between the copper plates 310 of the PCB and the shielded portion 320 of the PCB, $A_1$ refers to the area of the copper plate 310 of the PCB in square inches and $d_1$ refers to the thickness of the insulator situated between the copper plates 310 and the shielded portion 320. It is noted that there are no critical dimensions for the distance between the sensor plates and the acceptable range and any reasonably applicable range of distances may be utilized therein.

In a second step, the following formula may be used to calculate the capacitance of the full sensor just prior to performing the thermal ablation procedure:

$$C_2 = (0.118 * K_2 A_2)/d_2 + C_1$$

where $C_2$ refers to the capacitance, $K_2$ refers to the dielectric constant of the cassette, $A_2$ refers to the area of the copper plate 310 in square inches and $d_2$ refers to the thickness of the cassette.

As the amount of ablation fluid received in the cassette increases, the overall capacitance changes. As would be understood by those skilled in the art, that although this capacitance change is substantially linear when the plates are rectangular, the actual charging and discharging of capacitors is non-linear, due, in part, to factors including leakage, dissipation, manufacturing quality, equivalent series resistance, dielectric absorption, temperature dependence, etc. Accordingly, the system of the present invention is preferably altered to compensate for the non-linearity of the Capacitive Level Sensor 300. One such alteration may be the employment of tapered sensor plates rather than rectangular sensor plates. Alternately, the system may utilize software linearization, as those skilled in the art will understand.

The insulator situated between the sensor plates 310 and the shield 320 may be composed of a plastic foam tape approximately 0.05 inches thick with a copper plate area of 3.5 square inches. The cassette may be composed of an Acrylonitrile Butadiene Styrene ("ABS") plastic and have a thickness of 0.02 inches with a copper plate area of 3.5 square inches.

The resolution of the Capacitive Level Sensor 300 is a function of the measurement circuit, as shown in FIG. 4, and the capacitance range. The exemplary embodiment, as described, may have a resolution of approximately 1 part in 100. The design of the circuit of the exemplary embodiment of the present invention permits the fluctuation of the capacitance range to one half its present range without impacting the sensor resolution.

The circuit of the Capacitive Level Sensor 300 measures the capacitance regularly (e.g., approximately every 780 ms) and outputs a pulse-width modulated ("PWM") signal having the same period. The PWM signal is filtered with a 100 ms time constant, which settles within 500 ms, as those skilled in the art will understand.

The power supply for the aforementioned circuit may be an Analog to Digital ("A/D") converter that reads the sensor output in ratio-metric mode, as those skilled in the art will understand. Employment of the ratio-metric mode may supply a resultant voltage that is a ratio of the reference voltage, which may be accomplished by using the reference voltage as a source of excitation of the input voltage. By using a ratio-metric mode, supply induced output voltage changes may be avoided, thereby adding a degree of stability to the power source.

The present invention has been described with reference to specific exemplary embodiments. Those skilled in the art will understand that various modifications and changes may be made to the embodiments. The specifications are, therefore, to be regarded in an illustrative rather than a restrictive sense.

Those skilled in the art will understand that the described exemplary embodiments of the present invention may be altered without departing from the spirit or scope of the invention. Thus, it is to be understood that these embodiments have been described in an exemplary manner and are not intended to limit the scope of the invention which is intended to cover all modifications and variations of this invention that come within the scope of the appended claims and their equivalents.

What is claimed is:

1. A device for measuring an amount of ablation fluid circulating in an ablation system, comprising:
    a printed circuit board insertable into a fluid chamber of the ablation system and having a first surface and a second surface;
    first and second contacts provided adjacent first and second edges of the first surface;
    third and fourth contacts provided adjacent first and second edges of the second surface; and
    a data processing arrangement coupled to the printed circuit board and configured to measure a first conductivity between the first and third contacts and a second conductivity between the second and fourth contacts, the data processing arrangement determining a fluid level of the ablation fluid based on a comparison of the first and second conductivity measurements.

2. The device of claim 1, wherein the data processing arrangement is configured to indicate a fault if the first conductivity measurement differs from the second conductivity measurement by a value exceeding a predetermined threshold.

3. The device of claim 2, wherein the data processing arrangement is configured to output a pulse level sequence indicating a type of fault determined by the comparison.

4. The device of claim 1, wherein the data processing arrangement is configured to detect a fluid property of the fluid to determine a presence of an unwanted fluid in the ablation system.

5. The device of claim 4, further comprising a first test component provided in a test path between the first and third contacts and a second test component provided in a test path between the second and fourth contacts, the first and second test components being configured to detect a presence of the unwanted fluid.

6. The device of claim 1, wherein the contacts are gold-plated.

7. The device of claim 1, wherein the first contact is longitudinally offset from the second contact along the first surface.

* * * * *